US008603503B2

(12) United States Patent
Dias et al.

(10) Patent No.: US 8,603,503 B2
(45) Date of Patent: Dec. 10, 2013

(54) BILIQUID FOAMS STABLE DISPERSIONS THEREOF AND A CORRESPONDING PROCESS OF MANUFACTURING

(75) Inventors: Monica Dias, Guildford Surrey (GB); Philip Guffogg, Truro Cornwall (GB); Derek Wheeler, Beare Green Surrey (GB); Mark Whitbread-Jordan, Truro (GB)

(73) Assignee: Drug Delivery Solutions Limited, Leatherhead Surrey (GB)

( * ) Notice: Subject to any disclaimer, the term of this patent is extended or adjusted under 35 U.S.C. 154(b) by 1810 days.

(21) Appl. No.: 10/566,210

(22) PCT Filed: Jul. 30, 2004

(86) PCT No.: PCT/GB2004/003318
§ 371 (c)(1),
(2), (4) Date: May 2, 2006

(87) PCT Pub. No.: WO2005/011643
PCT Pub. Date: Feb. 10, 2005

(65) Prior Publication Data
US 2006/0239947 A1    Oct. 26, 2006

(30) Foreign Application Priority Data
Jul. 30, 2003   (GB) .................................. 0317868.8

(51) Int. Cl.
*A61K 8/02*    (2006.01)
*A61K 9/00*    (2006.01)

(52) U.S. Cl.
USPC ............ 424/401; 424/400; 514/945; 514/975

(58) Field of Classification Search
USPC .......................... 514/945, 975; 424/400, 401
See application file for complete search history.

(56) References Cited

U.S. PATENT DOCUMENTS

| | | | | |
|---|---|---|---|---|
| 4,001,392 A | * | 1/1977 | Curry et al. | 424/47 |
| 4,486,333 A | * | 12/1984 | Sebba | 516/14 |
| 4,999,198 A | | 3/1991 | Barnett et al. | |
| 5,980,970 A | | 11/1999 | Sattler et al. | |
| 6,165,479 A | | 12/2000 | Wheeler | |
| 6,235,067 B1 | * | 5/2001 | Ahern et al. | 44/301 |

FOREIGN PATENT DOCUMENTS

| | | | |
|---|---|---|---|
| EP | 487735 | | 6/1992 |
| EP | 960930 A1 | * | 12/1999 |
| GB | 2310813 | | 9/1997 |
| WO | 0162214 | | 8/2001 |
| WO | WO 03064024 A1 | * | 8/2003 |

OTHER PUBLICATIONS

Flick, Emulsifying Agents—An Industrial Guide, William Andrew Publishing/Noyes, 1990, p. 61 and 92.*
Knothe, Inform, 2001, 12, pp. 1103-1107.*
Merriam-Webster Dictionary, obtained online at: http://www.merriam-webster.com/dictionary.fuel, obatined online on Oct. 3, 2009.*

* cited by examiner

*Primary Examiner* — Abigail Fisher
(74) *Attorney, Agent, or Firm* — Novak Druce Connolly Bove + Quigg LLP

(57) ABSTRACT

A biliquid foam includes from 10% to 98% by weight of a non-polar liquid other than a fuel and from 2 to 88% by weight of a continuous phase polar liquid comprising a $C_1$-$C_4$ alcohol, a liquid polyethylene glycol, ethylene glycol or propylene glycol, or mixtures thereof, in an amount of at least 65% by weight, relative to the weight of the continuous phase, wherein the biliquid foam is stabilized with an amount of from 0.05% to 2% by weight based on the total formulation of a surfactant which is selected from castor oil/poly(alkylene glycol) adducts containing from 20 to 50 alkoxy groups, a $C_8$-$C_{24}$ fatty acid or hydrogenated castor oil/poly(alkylene glycol) adducts containing from 20 to 60 alkoxy groups, or mixtures thereof.

20 Claims, No Drawings

BILIQUID FOAMS STABLE DISPERSIONS THEREOF AND A CORRESPONDING PROCESS OF MANUFACTURING

BACKGROUND OF THE INVENTION

1. Field of the Invention

The present invention relates to biliquid foams with a high alcohol content and to products which are formulated therefrom.

2. The Prior Art

Biliquid foams are known in the art in which small droplets of a non-polar liquid such as an oil are encapsulated in a surfactant-stabilized film of a hydrocarbon bonded liquid, such as water, and separated from one another by a thin film of the hydrogen bonded liquid. The water or other hydrogen bonded liquid thus forms the continuous phase in biliquid foam compositions.

U.S. Pat. No. 4,486,333 to Sebba discloses a method for the preparation of biliquid foam compositions which may comprise the non-polar liquid in a total amount of about 60% to about 98% by volume, the hydrogen bonded liquid constituting the balance. The polar liquid may comprise a petroleum derivative, paraffin or a liquid halogenated hydrocarbon. The biliquid foam composition prepared comprising 96% by volume methanol and 4% by volume water had a limited stability of only several days.

Biliquid foams are disclosed in the following literature references by Sebba:

"Biliquid Foams", J. Colloid and Interface Science, 40 (1972) 468-474; and "The Behaviour of Minute Oil Droplets Encapsulated in a Water Film", Colloid Polymer Sciences, 257 (1979) 392-396.

WO 97/32559 discloses a stable dispersion comprising an oil-based biliquid foam and an aqueous gel which is suitable for use in cosmetics, pharmaceuticals and other industries. This patent specification does not describe the use of high levels of alcohols in the compositions.

U.S. Pat. No. 4,999,198 disclosed a biliquid foam (or polyaphron) having a continuous aqueous phase and a disperse phase in which a drug is carried in the disperse phase. This patent does not disclose the use of alcohol in the aqueous phase.

There is a need to generate aqueous products with high levels of alcohol, in particular in the cosmetic and personal care markets. This need is not, however, addressed by conventional emulsion science because of the instability of emulsions containing high levels of alcohol in the aqueous phase. There is also a need to generate topical oil-based products with a high level of alcohol, which increases skin permeability, but which products do not suffer from the disadvantage of the resulting skin dryness.

SUMMARY OF THE INVENTION

We have now found that high levels of alcohol can be incorporated into biliquid foams by formulating the compositions using particular selected surfactants. We have also found that these biliquid foams can be formulated with structuring agents, such as aqueous gels, to give compositions with a desired rheology.

Accordingly, the present invention provides a biliquid foam comprising or consisting of from 10% to 98% by weight of a non-polar liquid other than a fuel and from 2 to 88%, preferably 2 to 87%, by weight of a continuous phase polar liquid comprising a $C_1$-$C_4$ alcohol, a liquid polyethylene glycol, ethylene glycol or propylene glycol, or mixtures thereof in an amount of at least 65% by weight relative to the weight of the continuous phase, wherein the biliquid foam is stabilized with an amount of from 0.05% to 2% by weight, preferably 0.5% to 2% by weight, based on the total formulation of a surfactant which is selected from castor oil/poly(alkylene glycol) adducts containing from 20 to 50 alkoxy groups, a $C_8$-$C_{24}$ fatty acid or hydrogenated castor oil/poly(alkylene glycol) adducts containing from 20 to 60 alkoxy groups, or mixtures thereof.

The non-polar liquid can include mineral oil, a siloxane, an emollient ester, a glyceride, a lanolin oil, a natural oil, oleyl alcohol, isoeicosane, isooctahexacontane, or mixtures thereof. The siloxane can include dimethicone, cyclomethicone, dimethiconol, dimethicone copolyol, octamethylcyclotetrasiloxane, octamethylcyclo-pentasiloxane, decamethylcyclopentasiloxane, or mixtures thereof. The emollient ester can be isopropyl isostearate, lanolate, myristate or palmitate, or octyl palmitate, or mixtures thereof.

The polar liquid is preferably aqueous and comprises from 65% to 99% by weight, preferably 70% to 99% by weight, of the $C_1$-$C_4$ alcohol, liquid polyethylene glycol, ethylene glycol or propylene glycol, or mixtures thereof. The preferred $C_1$-$C_4$ alcohol for use in the invention is ethanol.

The liquid polyethylene glycol is a polyethylene glycol which is liquid at room temperature (22° C.). It may, for example, contain from 1 to 12 ethylene oxide units or may, for example, have a molecular weight of up to 600.

The particular classes of surfactant used in the present invention have been selected for use because of their ability to assist in the preparation of the biliquid foam compositions and because they impart good stability upon the majority of the biliquid foam compositions of the present invention prepared using them. The castor oil/poly(alkylene glycol) adducts generally impart a stability of up to 45 days, whilst the hydrogenated castor oil/poly(alkylene glycol) adducts generally impart a good long term stability of from 30 to 90 days.

The preferred classes of surfactants for use in the present invention are hydrogenated castor oil/polyethylene glycol adducts containing from 25 to 60 ethoxy groups, more preferably 40 to 60 ethoxy groups or castor oil/polyethylene glycol adducts containing from 25 to 45 ethoxy groups.

The $C_8$-$C_{24}$ fatty acid may be saturated or unsaturated. Preferred are $C_{12}$-$C_{22}$ fatty acids, especially oleic acid, linoleic acid and linolenic acid.

It will be understood by those skilled in the art that the choice of surfactant will also depend upon the particular non-polar liquid and the particular polar liquid and the amount thereof which are used in the preparation of the biliquid foams.

The surfactant which is used in the present invention may be used in combination with an appropriate co-surfactant. Examples of co-surfactants which may be used are polyoxyethylene oleyl ethers and hydrogenated castor oil/polyethylene glycol (25) adduct.

The preferred amount of surfactant for use in the present invention is about 1% by weight based on the total formulation.

The biliquid foam compositions of the present invention may also contain other additives such as preservatives (for instance to prevent microbiological spoilage). These additives may be included in the non-polar liquid or the continuous phase.

It will be understood that the inclusion of these additives will be at the levels and with the type of materials which are found to be effective and useful. Care needs to be taken in the choice and amount of these additives to prevent compromise to the other performance advantages of the present invention.

Methods of producing biliquid foams are described in U.S. Pat. No. 4,486,333 involving the preliminary formation of a gas foam in order to provide a sufficiently large surface area on which the biliquid foam can subsequently be formed. It has been found that the prior formation of a gas foam is not required to manufacture a stable biliquid foam, provided that a suitable stirring mechanism is provided in the manufacturing vessel. An important aspect of the present invention is the ability to manufacture biliquid foams without the preliminary formation of gas foam, by the use of a tank incorporating a suitable stirring mechanism.

Such an apparatus comprises a tank provided with a stirrer in which the stirrer blade breaks the interface between the liquid and air. A delivery device is provided through which the oil phase (non-polar liquid), which will comprise the internal phase of the dispersion is delivered to the tank. The design of the delivery device is such that the rate of addition of the internal phase fluid can be controlled and varied during the production process. A feature of the production process is that the internal (oil) phase is added to the stirred aqueous phase slowly at first until sufficient droplets have been formed to constitute a large, additional surface area for the more rapid formation of new droplets. At this point, the rate of addition of the oil phase may be increased.

The production process consists of the following steps:
1. The addition of one or more chosen surfactants to one or other or both phases (as previously determined by experiment).
2. The charging of the aqueous phase into the bottom of a process vessel.
3. The incorporation of the stirrer into the vessel so that it stirs the surface of the aqueous phase.
4. Adjustment of the stirrer speed to a previously determined level.
5. The slow addition of the internal phase whilst continuing to stir at the prescribed speed.
6. The speeding up of the rate of addition of the oil phase once a prescribed amount (usually between 5% and 10% of the total amount to be added) has been added.

The stirring rate and the rate of addition of the oil phase are variables, the values of which depend upon the detailed design of the manufacturing plant (in particular, the ratio of tank diameter to impeller diameter), the physico-chemical properties of the oil phase and the nature and concentrations of the chosen surfactants. These can all be pre-determined by laboratory or pilot plant experiment.

It will be understood by those skilled in the art that other manufacturing methods may be used, as appropriate.

The high alcohol biliquid foams of the present invention may be stabilized by means of an aqueous gel and, accordingly, the present invention includes within its scope a stable dispersion having a content of $C_1$-$C_4$ alcohol, a liquid polyethylene glycol, ethylene glycol or propylene glycol, or mixtures thereof, of at least 65% by weight, which dispersion comprises from 1 to 80% by weight of a biliquid foam and from 20 to 99% by weight of an aqueous gel.

The present invention provides a process for preparing a stable dispersion which comprises from 1 to 50% by weight of a biliquid foam as defined above and from 99% to 20% by weight of an aqueous gel, which process comprises mixing together the biliquid foam and the aqueous gel. Preferably, the dispersion has a content of $C_1$-$C_4$ alcohol, liquid polyethylene glycol, ethylene glycol or propylene glycol, or mixtures thereof at least 65% by weight. Preferably, the aqueous gel constitutes 50% of the stable dispersion.

The aqueous gel will preferably be formed from a colloidal polymer or gum suspended in water, at a concentration of from 0.05 to 20% by weight, more preferably from 0.2 to 1% by weight. Suitable polymers or gums are, for example, alginate gums or their salts, guar gum, locust bean gum, xanthan gum, gum acacia, gelatin, hydroxymethylcellulose or its hydroxyethylcellulose, hydroxypropylcellulose, carboxymethylcellulose or its salts, bentonites, magnesium aluminium silicates, "Carbomers" (salts of cross-linked polymers of acrylic acid), or glyceryl polymethacrylates or their dispersions in glycols, or any appropriate mixture of any of these polymers and gums. Preferred gelling agents are those which confer plastic behaviour on the aqueous phase, that is, under their influence, any shear stress applied to the product must attain a minimum yield value before any liquid flow takes place.

The stable dispersions of the present invention may be used to formulate pharmaceutical or cosmetic compositions, for example, pharmaceutical or cosmetic compositions for topical application. Examples of active ingredients which may be included in such compositions are acyclovir, beclometasone, benzoyl peroxide, benzydamine, betamethasone valerate, caffeine, calamine, cetrimide, chlortetracycline, clobetasol, clobetasone, clotrimazole, crotamiton, diclofenac, diethylamine salicylate, diflucortolone, dithranol, econazole, erythromycin, fluocinolone, fluocinonide, flucortolone, fluorouracil, fluticasone, fusidic acid, felbinac, ketoprofen, gentamicin, hydrocortisone, hydrocortisone acetate, ibuprofen, isotretinoin, lactic acid, lidocaine/lignocaine, lidocaine and chlorhexidine/lignocaine and chlorhexidine, macrogol, methyl salicylate, metronidazole, mexenone, miconazole, nystatin, piroxicam, potassium hydroxy-quinoline sulphate and benzoyl peroxide, retinoic acid and its derivatives, salicylic acid, sodium fusidate, coal tar and salicylic acid, coal tar and zinc, tetracyclin, titanium, tretinoin, triamcinolone, tioconazole, triamcinolone, triclosan, urea, zinc, zinc and ichthammol, and mixtures thereof.

The drug concentration will vary, depending upon the drug used, from about 0.01% to 10% by weight. Hence, the compositions of the present invention comprise a safe and effective amount of the active ingredient.

The stable dispersions of the present invention may therefore be used to formulate the following compositions for use in the pharmaceutical or cosmetics industry.

Topical Compositions

The alcohol which is preferably contained in the biliquid foams used in the present invention enhances the permeation through the skin of the active ingredient(s). The biliquid foam delivers oils to the skin and this helps to overcome skin dryness associated with topical compositions containing alcohol and to restore the barrier properties of the skin.

Topical applications may comprise the delivery of drugs, such as NSAIDS or anti-acne compositions, in a cream or gel preparation, or the delivery of drugs such as nicotine, estradiol, nitroglycerin, testosterone, scopolamine, etc., via transdermal drug delivery devices or in a cream or gel preparation. Another topical application comprises the delivery of cosmeceutical products, such as anti-cellulite creams formulated with an active ingredient, such as caffeine, to the skin. The active ingredient will have an enhanced performance due to the skin enhancer effect of the alcohol. Another topical product is an aftershave lotion.

Hand Disinfectants

Hand disinfectants formulated using the stable suspensions of the present invention have bactericidal properties provided by the high levels of alcohol contained in the compositions. The combination in the same product of the alcohol and oils avoids the skin dryness which is a disadvantage of existing high alcohol disinfectant compositions.

The present invention will be further described with reference to the following Examples:

Biliquid Foam Preparation

A suitable vessel is charged with the aqueous phase of the biliquid foam. The oil phase was added at a constant rate with stirring, using a sweep stirrer or an orbital mixer. After completion of the oil addition, the stirring was continued until the size of the oil droplets became stable or reached a desired size.

Stable Dispersion Preparation

In a separate vessel the aqueous gel phase components were combined to produce an aqueous gel. The biliquid foam was combined with the aqueous gel under low shear stirring until a homogenous product was produced.

EXAMPLE 1

|  | % (w/w) |
|---|---|
| oil phase | |
| Mineral Oil | 90.0 |
| aqueous phase | |
| Hydrogenated Castor Oil/Polyoxyethylene Glycol (60) adduct | 1.0 |
| Ethanol | 7.0 |
| Water | 2.0 |
| | 100.0 |

Ethanol % of continuous polar phase = ~78%
Surfactant % = 1
Stability - 20 months

EXAMPLE 2

|  | % (w/w) |
|---|---|
| oil phase | |
| Isopropyl Isostearate (IPIS) | 34.67 |
| Isoeicosane (Permethyl 102a) | 43.86 |
| Isooctahexacontane (Permethyl 104a) | 10.97 |
| aqueous phase | |
| Hydrogenated Castor Oil/Polyoxyethylene Glycol(25) adduct | 0.50 |
| Water | 2.60 |
| Ethanol | 7.00 |
| Polyoxyethylene(20)Oleyl Ether(Oleth20) | 0.40 |
| | 100.0 |

Ethanol % of continuous polar phase = ~73%
Surfactant % = 0.9
Stability - 20 months

EXAMPLE 3

|  | % (w/w) |
|---|---|
| oil phase | |
| Dimethicone Polydimethylsiloxane (DOW Corning 200/350 cs) | 8.06 |
| Dimethicone Polydimethylsiloxane (DOW Corning 200/5 cs) | 32.34 |
| Dimethicone Polydimethylsiloxane (DOW Corning 200/20 cs) | 24.30 |
| Dimethicone Polydimethylsiloxane (DOW Corning 200/30,000 cs) | 24.30 |
| Castor Oil/Polyoxyethylene Glycol(25) adduct | 0.50 |
| Castor Oil/Polyoxyethylene Glycol(15) adduct | 0.50 |
| aqueous phase | |
| Water | 2.50 |
| Ethanol | 7.50 |
| | 100.0 |

Ethanol % of continuous polar phase = 75%
Surfactant % = 1
Stability - 24 months

EXAMPLE 4

|  | % w/w) |
|---|---|
| oil phase | |
| Octamethylcyclopentasiloxane and organopolysiloxane (Gransil GCM) | 48.6 |
| Dimethicone and organopolysiloxane (Gransil TMG) | 22.5 |
| Dimethicone Polydimethylsiloxane (DOW Corning 200/50 cs) | 0.9 |
| Cetearyl isononanoate | 9.0 |
| Isopar K | 9.0 |
| aqueous phase | |
| Ethanol | 7.0 |
| Water | 2.0 |
| Hydrogenated castor oil/Polyoxyethylene Glycol(25) adduct | 1.0 |
| | 100.0 |

Ethanol % of continuous polar phase = ~78%
Surfactant % = 1.0
Stability - greater than 5 months

EXAMPLE 5

|  | % w/w |
|---|---|
| oil phase | |
| Isopropyl isostearate (IPIS) | 18.56 |
| Isoeicosane (Permethyl 102a) | 23.76 |
| Isooctahexacontane (Permethyl 104a) | 5.94 |
| Octamethylcyclotetra-siloxane and dimethiconol (Dow Corning 1401) | 11.14 |

-continued

|  | % w/w |
|---|---|
| Decamethylcyclopenta-siloxane (Dow Corning 245) | 11.14 |
| Dimethicone Polydimethylsiloxane (DOW Corning 200/100 cs) | 18.56 |
| Hydrogenated castor oil/Polyoxyethylene Glycol(25) adduct | 0.50 |
| Castor Oil/Polyoxyethylene Glycol(25) adduct | 0.50 |
| aqueous phase | |
| Ethanol | 7.50 |
| Water | 2.50 |
|  | 100.00 |

Ethanol % of continuous polar phase = 75%
Surfactant % = 1.0
Stability - 24 months

EXAMPLE 6

|  | % (w/w) |
|---|---|
| oil phase | |
| Cetearyl isononoanoate | 19.230 |
| Isoeicosane (Permethyl 102a) | 23.560 |
| Octamethylcyclotetra-siloxane (Dow Corning 1401) | 11.050 |
| Decamethylcyclopenta-siloxane (Dow Corning 245) | 11.050 |
| Isooctahexacontane (Permethyl 104a) | 5.890 |
| Dimethicone Polydimethylsiloxane (DOW Corning 200/100 cs) | 19.220 |
| aqueous phase | |
| Ethanol | 7.000 |
| Water | 2.000 |
| Hydrogenated Castor Oil/Polyoxyethylene Glycol (25) adduct | 0.625 |
| Castor Oil/Polyoxyethylene Glycol(25) adduct | 0.375 |
|  | 100.00 |

Ethanol % of continuous polar phase = 78%
Surfactant % = 1.0
Stability - greater than 1 month

EXAMPLE 7

|  | % (w/w) |
|---|---|
| oil phase | |
| Isopropoyl isostearate (IPIS) | 90.0 |
| aqueous phase | |
| Hydrogenated castor Oil/Polyoxyethylene Glycol(60) adduct | 1.0 |
| Ethanol | 7.0 |
| Water | 2.0 |
|  | 100.0 |

Ethanol % of continuous polar phase = 78%
Surfactant % = 1
Stability - greater than 20 months

EXAMPLE 8

|  | % (w/w) |
|---|---|
| oil phase | |
| Dimethicone Polydimethylsiloxane (Dow Corning 200/350) | 8.06 |
| Dimethicone Polydimethylsiloxane (Dow Corning 200/5) | 32.34 |
| Dimethicone Polydimethylsiloxane (Dow Corning 200/20) | 24.30 |
| Dimethicone Polydimethylsiloxane (Dow Corning 200/30000) | 24.30 |
| Hydrogenated castor oil/Polyoxyethylene Glycol (60) adduct | 1.00 |
| aqueous phase | |
| Ethanol | 8.00 |
| Water | 2.00 |
|  | 100.00 |

Ethanol % of continuous polar phase = 80%
Surfactant % = 1
Stability - 20 months

EXAMPLE 9

|  | % (w/w) |
|---|---|
| oil phase | |
| Mineral oil | 90.0 |
| aqueous phase | |
| Croduret 50 special | 1.0 |
| Ethanol | 7.0 |
| Water | 2.0 |
|  | 100.0 |

Ethanol % of continuous polar phase = 77.8%
Surfactant % = 1
Stability - >2 months

EXAMPLE 10

|  | % (w/w) |
|---|---|
| oil phase | |
| Mineral oil | 89.1 |
| Oleic acid | 0.9 |
| aqueous phase | |
| Croduret 50 special | 0.2 |
| Ethanol | 7.0 |
| Water | 2.8 |
|  | 100.0 |

Ethanol % of continuous polar phase = 71.4%
Surfactant % = 0.2
Surfactant + oleic acid % = 1.1
Stability - >2 months

EXAMPLE 11

|  | % (w/w) |
|---|---|
| oil phase | |
| Mineral oil | 90.0 |
| aqueous phase | |
| Croduret 50 special | 0.2 |
| Ethanol | 7.0 |
| Water | 2.8 |
| | 100.0 |

Ethanol % of continuous polar phase = 71.4%
Surfactant % = 0.2
Stability - >3 weeks

EXAMPLE 12

|  | % (w/w) |
|---|---|
| oil phase | |
| Mineral oil | 90.0 |
| aqueous phase | |
| Croduret 50 special | 0.1 |
| Ethanol | 7.0 |
| Water | 2.9 |
| | 100.0 |

Ethanol % of continuous polar phase = 70.7%
Surfactant % = 0.1%
Stability - >2 weeks

EXAMPLE 13

|  | % (w/w) |
|---|---|
| oil phase | |
| Mineral oil | 90.00 |
| aqueous phase | |
| Croduret 50 special | 0.05 |
| Ethanol | 7.00 |
| Water | 2.95 |
| | 100.00 |

Ethanol % of continuous polar phase = 70.35%
Surfactant % = 0.05
Stability - >2 weeks

EXAMPLE 14

|  | % (w/w) |
|---|---|
| oil phase | |
| Tegopren 6814 | 90.0 |
| aqueous phase | |
| Croduret 50 special | 1.0 |
| Propylene glycol | 8.1 |
| Water | 0.9 |
| | 100.0 |

Propylene glycol % of continuous polar phase = 90%
Surfactant % = 1
Stability - >6 weeks

EXAMPLE 15

|  | % (w/w) |
|---|---|
| oil phase | |
| Tegopren 6814 | 89.1 |
| Oleic acid | 0.9 |
| aqueous phase | |
| Croduret 50 special | 0.2 |
| Propylene glycol | 8.8 |
| Water | 1.0 |
| | 100.0 |

Propylene glycol % of continuous polar phase = 89.8%
Surfactant % = 0.2
Surfactant % including oleic acid = 1.1
Stability - >6 weeks

EXAMPLE 16

|  | % (w/w) |
|---|---|
| oil phase | |
| Mineral oil | 89.1 |
| Oleic acid | 0.9 |
| aqueous phase | |
| Protachem CAH-25 | 0.2 |
| Ethanol | 7.0 |
| Water | 2.8 |
| | 100.0 |

Ethanol % of continuous polar phase = 71.4%
Surfactant % = 0.2
Surfactant % including oleic acid = 1.1
Stability - >5 weeks

EXAMPLE 17

|  | % (w/w) |
| --- | --- |
| oil phase | |
| Soya bean oil | 89.0 |
| Hydrogenated castor oil/ polyoxyethylene glycol (40) adduct | 1.0 |
| aqueous phase | |
| Propylene glycol | 9.5 |
| Water | 0.5 |
|  | 100.0 |

Propylene glycol % of continuous polar phase = 95%  
Surfactant % = 1  
Stability - 3 months

EXAMPLE 18

|  | % (w/w) |
| --- | --- |
| oil phase | |
| Soya bean oil | 77.27 |
| aqueous phase | |
| Polyoxyethylene glycol (PEG 6) | 20.46 |
| Croduret 50 Special | 2.27 |
|  | 100.00 |

PEG 6% of continuous polar phase = 100%  
Surfactant % = 2.27  
Stability - 4 weeks

EXAMPLE 19

|  | % (w/w) |
| --- | --- |
| oil phase | |
| Waglinol 3/9280 | 89.0 |
| Hydrogenated castor oil/polyoxyethylene glycol (40) adduct | 1.0 |
| aqueous phase | |
| Propylene glycol | 9.5 |
| Water | 0.5 |
|  | 100.0 |

Propylene glycol as % of continuous polar phase = 95%  
Surfactant % = 1.0  
Stability - >3 months

EXAMPLE 20

|  | % (w/w) |
| --- | --- |
| oil phase | |
| Waglinol 3/9280 | 89.0 |
| Castor oil/polyoxyethylene glycol (40) adduct | 1.0 |
| aqueous phase | |
| Propylene glycol | 9.5 |
| Water | 0.5 |
|  | 100.0 |

Propylene glycol as % of continuous polar phase = 95%  
Surfactant % = 1.0  
Stability - >3 months

EXAMPLE 21

|  | % (w/w) |
| --- | --- |
| oil phase | |
| Soya bean oil | 89.0 |
| Castor oil/polyoxyethylene glycol (35) adduct | 1.0 |
| aqueous phase | |
| Propylene glycol | 9.0 |
| Water | 1.0 |
|  | 100.0 |

Propylene glycol as % of continuous polar phase = 90%  
Surfactant % = 1.0  
Stability - >3 months

EXAMPLES 22 TO 26

Gelled Formulations

Example 22 to 26 show that there is a wide range of polymers, which can be used to gel the biliquid foams. These polymer systems can be prepared at different concentrations of ethanol. Hence, the concentration of ethanol in the final formulations can also vary. All polymers were dispersed in a water/ethanol mixture using a high-shear rotorstator mixer (Silverson) and neutralizers were added as appropriate, to form polymer gels. The biliquid foams were prepared as discussed above. All ingredients were mixed together at room temperature.

EXAMPLE 22

|  | % (w/w) |
| --- | --- |
| Part A: Preparation of biliquid foam | |
| oil phase | |
| Isopropyl isostearate (IPIS) | 34.17 |
| Isoeicosane (Permethyl 102a) | 43.86 |
| Isooctahexacontane (Permethyl 104a) | 10.97 |

13
-continued

|  | % (w/w) |
| --- | --- |
| aqueous phase | |
| Hydrogenated castor oil/polyoxyethylene glycol (25) adduct | 0.50 |
| Water | 3.60 |
| Ethanol | 6.00 |
| Polyoxyethylene (20) oleyl ether (Oleth 20) | 0.40 |
| | 100.00 |
| Part B: Preparation of biliquid foam | |
| oil phase | |
| DC 200/350 | 8.06 |
| DC 200/5 | 32.34 |
| DC 200/20 | 24.30 |
| DC 200/30,000 | 24.30 |
| aqueous phase | |
| Castor oil/polyoxyethylene glycol (25) Adduct | 0.50 |
| Castor oil/polyoxyethylene glycol (15) Adduct | 0.50 |
| Water | 4.00 |
| Ethanol | 6.00 |
| | 100.00 |
| Part C: Preparation of gelled formulation | |
| Klucel HF | 0.30 |
| Lubrajel DV | 15.00 |
| Ethanol | 50.00 |
| Water | 22.70 |
| Biliquid Foam of Part A | 6.50 |
| Biliquid Foam of Part B | 5.50 |
| | 100.00 |

% ethanol on aqueous phase = 68

EXAMPLE 23

|  | % (w/w) |
| --- | --- |
| Carbomer 980 neutralised with TEA | 0.60 |
| Ethanol | 49.90 |
| Water | 32.66 |
| Biliquid Foam of Example 5 | 16.84 |
| | 100.00 |

EXAMPLE 24

|  | % (w/w) |
| --- | --- |
| Hydroxyethyl cellulose | 0.30 |
| Carbomer 980 neutralised with TEA | 0.45 |
| Ethanol | 49.00 |
| Water | 20.25 |
| Biliquid Foam of Example 1 | 30.00 |
| | 100.00 |

EXAMPLE 25

|  | % (w/w) |
| --- | --- |
| Biliquid foam of Example 6 | 16.68 |
| Carbomer 980 TEA | 1.20 |
| Sepigel | 0.50 |
| Ethanol | 57.16 |
| Water | 24.26 |
| | 100.00 |

EXAMPLE 26

|  | % (w/w) |
| --- | --- |
| Part A: - Biliquid foam preparation | |
| oil phase | |
| Isopropyl isostearate | 53.46 |
| Squalane | 35.64 |
| Laureth 4 | 0.90 |
| aqueous phase | |
| SLES in water (Sodium lauryl ether sulphate) | 10.00 |
| | 100.00 |
| Part B: - Gelled formulation | |
| Water | 0.79 |
| Triclosan | 0.10 |
| Ethanol | 70.00 |
| 2% Carbomer 980 (neutralised with AMP 95) | 20.00 |
| Opacifier | 1.00 |
| Sepigel | 2.50 |
| Biliquid foam of Part A | 5.61 |
| | 100.00 |

% ethanol on aqueous phase = 77%

Drug Formulations

Examples 27 and 28 were prepared from biliquid foam shown below. The actives were in both cases formulated in the gel phase. The Carbomer was dispersed in the water/ethanol mixture using a high-shear rotorstator mixer (Silverson). The drug was then added to the above mixture once the Carbomer was fully dispersed and an aqueous solution of 20% triethylamine (TEA) was added until a clear viscous gel at pH 7 was obtained. The biliquid foam (Example 4) was mixed with the polymer gel at room temperature until a semi viscous white gel was obtained.

EXAMPLE 27

|  | % (w/w) |
| --- | --- |
| Preparation of biliquid foam A | |
| oil phase | |
| Gransil GCM | 48.60 |
| Gransil DMG | 22.50 |
| DC200 (50 cs) | 0.90 |

-continued

| | % (w/w) |
|---|---|
| Ceterayl Isononanoate | 9.00 |
| Isopar K | 9.00 |
| aqueous phase | |
| Ethanol | 5.67 |
| Water | 2.43 |
| Hydrogenated castor oil/Polyoxyethylene glycol (25) adduct | 0.90 |
| | 100.00 |
| preparation of gelled formulation | |
| Composition | |
| Biliquid foam A | 30.000 |
| Caffeine | 3.080 |
| 1% Natrasol | 0.238 |
| 1% Carbomer | 0.154 |
| Butylene glycol | 2.800 |
| Kathon CG (0.4%) | 2.800 |
| Sodium hyaluronate (1%) | 2.800 |
| Water | 29.064 |
| Ethanol | 29.064 |
| Total | 100.000 |

EXAMPLE 28

| | % (w/w) |
|---|---|
| Preparation of biliquid foam B | |
| oil phase | |
| Mineral Oil | 90.00 |
| aqueous phase | |
| Ethanol | 7.07 |
| Water | 2.13 |
| Hydrogenated castor oil/Polyoxyethylene glycol (25) adduct | 0.80 |
| | 100.00 |
| preparation of gelled formulation | |
| Composition | |
| Biliquid foam B | 30.000 |
| Water | 18.4769 |
| Ethanol | 42.0400 |
| Ibuprofen | 9.3200 |
| Aristoflex AVC | 0.1625 |
| Euxyl K400 | 0.0006 |
| Total | 100.0000 |

Footnotes to the Examples

In all cases the following were used:
Water—demineralized water
Ethanol—DEB 100
Isopar K—C13-C15 Isoparaffin
Klucel HF—Hydroxypropyl cellulose
Lubragel DV—Polymethacrylate propylene glycol
Sepigel—Polyacrylamid/C13-C14 isoparaffin laureth-7
Natrosol 250 HHR—Hydroxyethyl cellulose
Kathon CG—Methylchloroisothiozolanone and methylisothiazolinone
Croduret 50 Special—Hydrogenated castor oil/polyethylene glycol (40-50) adduct supplied by Croda Chemicals Limited.
TEA—Triethanolamine.
Carbomer 980—Polyacrylic acid used as thickener when neutralized with a base.
Waglinol 3/9280—Caprylic-capric triglyceride (CCT)
Protachem CAH-25—Hydrogenated castor oil/polyethylene glycol (25) adduct supplied by Protameen Chemicals Inc.
PEG 6—Polyoxyethyleneglycol (6), also known as PEG 300.
Tegopren 6814—Alkyl polydimethylsiloxane supplied by Th. Goldschmidt AG.
AMP-95—2-amino-methyl-1-propanol containing 5% water.

We claim:

1. A biliquid foam comprising;
   from 10% to 98% by weight of a non polar liquid comprising a mineral oil, a siloxane, an emollient ester, a glyceride, a lanolin oil, a natural oil, oleyl alcohol, isoeicosane or isooctahexacontane, or mixtures thereof; and
   from 2 to 88% by weight of a continuous phase polar liquid comprising a $C_1$-$C_4$ alcohol, a liquid polyethylene glycol, ethylene glycol or propylene glycol, or mixtures thereof, in an amount of at least 65% by weight, relative to the weight of the continuous phase,
   wherein the biliquid foam is stabilized with an amount of from 0.05% to 2% by weight based on the total formulation of a surfactant which is selected from the group consisting of castor oil/poly(alkylene glycol) adducts containing from 20 to 50 alkoxy groups, a $C_8$-$C_{24}$ fatty acid or hydrogenated castor oil/poly(alkylene glycol) adducts containing from 20 to 60 alkoxy groups, or mixtures thereof.

2. The biliquid foam as claimed in claim 1, wherein the amount of surfactant is about 1% by weight based on the total formulation.

3. The biliquid foam as claimed in claim 2, wherein the surfactant comprises a hydrogenated castor oil/polyethylene glycol adduct containing from 40 to 60 ethoxy groups.

4. The biliquid foam as claimed in claim 2, wherein the surfactant comprises a castor oil/poly(alkylene glycol) adduct containing 25 to 45 ethoxy groups.

5. The biliquid foam as claimed in claim 1, wherein the siloxane comprises dimethicone, cyclomethicone, dimethiconol, dimethicone copolyol, octamethylcyclotetrasiloxane, octamethylcyclo-pentasiloxane, decamethylcyclopentasiloxane, or mixtures thereof.

6. The biliquid foam as claimed in claim 1, wherein the emollient ester is isopropyl isostearate, lanolate, myristate or palmitate, or octyl palmitate, or mixtures thereof.

7. The biliquid foam as claimed in claim 1, wherein the surfactant comprises a hydrogenated castor oil/polyethylene glycol adduct containing from 40 to 60 ethoxy groups.

8. The biliquid foam as claimed in claim 1, wherein the surfactant comprises a castor oil/poly(alkylene glycol) adduct containing 25 to 45 ethoxy groups.

9. The biliquid foam as claimed in claim 1, wherein the polar liquid is aqueous and comprises from 70% to 99% by weight of the $C_1$-$C_4$, alcohol, liquid polyethylene glycol, ethylene glycol or propylene glycol, or mixtures thereof.

10. A stable dispersion comprising from 1 to 80% by weight of a biliquid foam as claimed in claim 1, and from 99 to 20% by weight of an aqueous gel.

11. The stable dispersion as claimed in claim 10, wherein the aqueous gel constitutes from 50 to 99% by weight thereof.

12. The stable dispersion as claimed in claim 10, wherein the aqueous gel comprises a colloidal polymer or gum suspended in water.

13. The stable dispersion as claimed in claim 10 which includes therein at least one pharmaceutical or cosmetic compound therein.

14. A process for preparing a stable dispersion which comprises from 1 to 80% by weight of a biliquid foam as claimed in claim 1, and from 99 to 20% by weight of an aqueous gel, which process comprising mixing together the biliquid foam and the aqueous gel.

15. A process as claimed in claim 14, wherein the stable dispersion also comprises a pharmaceutical compound.

16. A process as claimed in claim 15 in which the stable dispersion is in a topical form for application to the skin and contains a non steroidal anti-flammatory drug, an anti-acne compound, anti-viral or anti-bacterial compound.

17. A process as claimed in claim 15 in which the stable dispersion is in the form of a transdermal delivery device or in a cream or gel preparation and which contains nicotine, estradiol, nitroglycerin, testosterone or scopolamine as the active ingredient.

18. A process as claimed in claim 14, wherein the stable dispersion also comprises a cosmetic compound.

19. A process as claimed in claim 18 in which the stable dispersion is an anti-cellulite cream or an aftershave lotion.

20. A process as claimed in claim 14, wherein the stable dispersion also comprises a disinfectant compound.

* * * * *